United States Patent [19]

Buendia et al.

[11] Patent Number: 5,399,727
[45] Date of Patent: Mar. 21, 1995

[54] PREPARATION OF Δ9(11) STEROID

[75] Inventors: Jean Buendia, Le Perreux sur Marne; Patrick Roussel, Thiais; Michel Vivat, Lagny sur Marne, all of France

[73] Assignee: Roussel-Uclaf, France

[21] Appl. No.: 71,501

[22] Filed: Jun. 2, 1993

[30] Foreign Application Priority Data

Jun. 19, 1992 [FR] France ............... 92 07460

[51] Int. Cl.6 ............................................... C07J 3/00
[52] U.S. Cl. ..................................................... 552/610
[58] Field of Search ......................................... 552/610

[56] References Cited

U.S. PATENT DOCUMENTS 4,127,596  11/1978  Beaton et al. ............... 552/640

FOREIGN PATENT DOCUMENTS 0263569   4/1988  European Pat. Off. .
0294911  12/1988  European Pat. Off. .
2387245  10/1978  France .

OTHER PUBLICATIONS

1990 Butterworth Publishers, Steroids, 1990, vol. 55, Mar. (Jacobus N. Batist, et al) The Chemistry of 9-alpha-hydroxysteroids. 3. Methods . . . -3-one (pp. 109–113).

*Primary Examiner*—Howard T. Mars
*Assistant Examiner*—Rebecca Cook
*Attorney, Agent, or Firm*—Bierman and Muserlian

[57] ABSTRACT

A process for the preparation of a compound of the formula

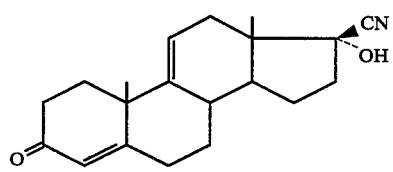

comprising reacting a compound of the formula

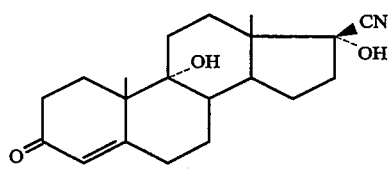

with chlorosulfonic in an organic solvent wherein the reaction is effected at −20° C. to −10° C. and the temperature is then allowed to rise to 0° C. to 5° C.

5 Claims, No Drawings

PREPARATION OF Δ9(11) STEROID

STATE OF THE ART

Known processes for preparing the compound of Formula I have generally consisted of either treating a 17-keto steroid with a Δ9(11)-double bond already present with alkali metal cyanide in an acetic acid-alkanol mixture or with acetone cyanohydrin in the presence of sodium hydroxide and water as described in U.S. Pat. No. 4,548,748, Japanese Patents No. 82 62299 and 8262300, Chem. Abs., Vol 97, No. 141,P.141–142 and Bull. Chem. Soc. Japan, Vol 58(3), p. 978 (1985). Another process consisted of dehydrating a 9,17α-diol-17β-cyano steroid with sulfuric acid or a BF$_3$-Et$_2$O complex as described in U.S. Pat. No. 4,921,638, European patent application No. 263,569 and Steroids, Vol 55(3), p. 109 (1990).

These dehydration processes using sulfuric acid are not practical on an industrial level due to the low yield that they produce, a part of the starting product being converted into an amide. As for the process using the BF$_3$ Et$_2$O complex, it produces a good yield, but it also cannot be used on an industrial level, due to the very large quantity of BF$_3$-Et$_2$O complex which would be necessary (see p. 111 "method D" of the Steroids reference mentioned above). 2 parts by weight of complex relative to the steroid used are required, which condition, added to the price of this reagent, completely rules it out.

OBJECTS OF THE INVENTION

It is an object of the invention to provide a novel economical process for the preparation of the compound of Formula I.

This and other objects and advantages of the invention will become obvious from the detailed description.

THE INVENTION

The novel process of the invention for the preparation of a compound of Formula

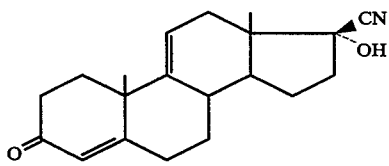

I comprises reacting the compound of Formula:

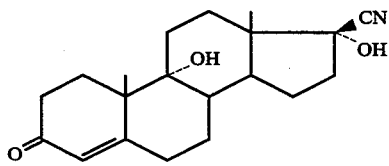

II with chlorosulfonic acid in an organic solvent.

In a preferred embodiment of the process of the invention, the operation is carried out in a polar aprotic solvent selected from the group consisting of tetrahydrofuran, dioxane, acetone, ethyl acetate, and methylene chloride, tetrahydrofuran and acetone being preferred. The reaction is carried out first at a temperature of −20° C. to −10° C., preferably −15° C., then by allowing the temperature to rise to between 0° and 10° C., preferably 5° C.

Chlorosulfonic acid has been used as a dehydration agent in steroid series to prepare Δ9(11) compounds from corresponding 9α-OH compounds (see French Patent 2,387,245). However, it should be noted, and this is essential, that the reaction is carried out on a single particular type of compound, namely compounds containing as the only substituents 3 and 17 oxo groups or methyl or fluoro radicals, i.e. compounds which do not contain any other hydroxy substituents, and which are thus not able to produce competitive reactions between the dehydration in position 9(11), which may itself moreover be in competition with a dehydration in position 8(9), and the dehydration at the carrier site of the other hydroxy substituent. The compound of Formula II, used at the start of the process of the present invention contains this other hydroxy substituent in the 17α-position.

It is known, notably from European Application 263,569 or from the Steroids article already mentioned, that in such cases, the use of dehydration reagent of the same type, namely methane sulfonic chloride, leads selectively, via an intermediate 17α-sulfonate, to the Δ16(17) derivative and not to the Δ9(11) derivative or to a mixture of the two. It can therefore be concluded that the selective result of the invention, with an excellent yield of the Δ9(11) derivative, was not foreseeable. The prior art taught that it was expected to obtain the Δ16(17) derivative, or at least a Δ9(11) and Δ16(17) mixture. It is certain that from an industrial point of view, it is indispensable to obtain selectively and with a high yield the desired Δ9 (11) derivative.

The selectivity of the process of the invention depends on the conditions under which it is carried out. The sulfonate is first formed selectively at an appropriate temperature, the rise in temperature being then necessary for the elimination leading to the formation of the Δ9(11) double bond. It prevents the formation of the Δ16(17) double bond which, as can be seen from the above, is easily produced.

The compound of Formula I described in European Application 263,569 is a useful intermediate especially in the synthesis of corticosteroids. The starting compound of Formula II is also described in this Application.

In the following example, there is described a preferred embodiment to illustrate the invention. However, it is to be understood that the invention is not intended to be limited to the specific embodiment.

EXAMPLE

17β-cyano-Δ4,9(11)-androsta-dien-17α-ol-3-one 2 g of 17β-cyano-Δ4-androsten-9α,17α-diol-3-one and 10 ml of tetrahydrofuran were mixed together under an anhydrous inert gas atmosphere and the mixture was then cooled to −15° C. 0.5 ml of chlorosulfonic acid were introduced at this temperature during one hour, the mixture was stirred, and the temperature was allowed to rise to 5° C. over a period of 30 minutes. The mixture was held at this temperature for 90 minutes and then 10 g of ice and 10 ml of ice-cooled water were added. After 30 minutes, another 10 ml of ice-cooled water were added and the mixture was stirred for one hour at 0° C. Separation was carried out and the crystals were washed with water, then dried to obtain 1.72 g of the expected product melting at 247° C. (Yield: 91%).

From the mother liquors, it was possible to isolate about another 3% of additional expected product.

IR Spectrum (CHCl₃) Absorptions at 3620 cm⁻¹ (OH), 3569 cm⁻¹ (SH) 1633 cm⁻¹ (>C=O), 1614 cm⁻¹ (C=C), 2238 cm⁻¹ (—C≡N).

NMR Spectrum (CDCl₃, 250 MHz, ppm) 0.95: H of CH₃ in position 13; 1.36: H of CH₃ in position 10; 5.59: H in position 11; 5.72: H in position 4; 7.57 H of OH.

Various modifications of the process of the invention may be made without departing from the spirit or scope thereof and it is to be understood that the invention is intended to be limited only as defined in the appended claims.

What we claim is:

1. A process for the selective preparation of a compound of the formula

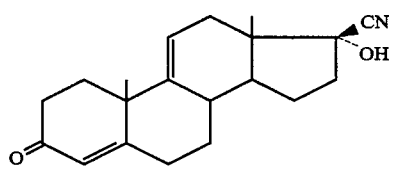

comprising reacting a compound of the formula

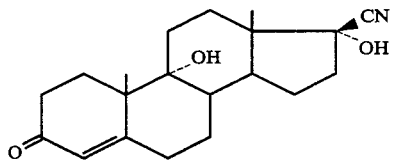

with chlorosulfonic acid in polar, aprotic solvent wherein the reaction is effect at −20° C. to −10° C. and the temperature is then allowed to rise to 0° C. to 5° C.

2. The process of claim 1 wherein the polar aprotic solvent is selected from the group consisting of tetrahydrofuran, dioxane, acetone, ethyl acetate, and methylene chloride.

3. The process of claim 1 wherein the polar aprotic solvent is tetrahydrofuran.

4. The process of claim 1 wherein the polar aprotic solvent is acetone.

5. The process of claim 1 wherein the reaction is effected at about −15° C. and the temperature is then allowed to rise to about 5° C.

* * * * *